(12) United States Patent
Aldridge et al.

(10) Patent No.: US 9,345,465 B2
(45) Date of Patent: May 24, 2016

(54) ACTUATOR FOR BAND TENSIONING SYSTEM

(71) Applicant: Dallen Medical, Inc., San Clemente, CA (US)

(72) Inventors: David Trottingwolf Aldridge, Laguna Hills, CA (US); Seth Arnold Foerster, San Clemente, CA (US)

(73) Assignee: Dallen Medical, Inc., San Clemente, CA (US)

( * ) Notice: Subject to any disclaimer, the term of this patent is extended or adjusted under 35 U.S.C. 154(b) by 611 days.

(21) Appl. No.: 13/740,044

(22) Filed: Jan. 11, 2013

(65) Prior Publication Data

US 2013/0184720 A1 Jul. 18, 2013

Related U.S. Application Data

(60) Provisional application No. 61/586,566, filed on Jan. 13, 2012.

(51) Int. Cl.
*A61B 17/04* (2006.01)
*A61B 17/88* (2006.01)
(Continued)

(52) U.S. Cl.
CPC .............. *A61B 17/04* (2013.01); *A61B 17/8861* (2013.01); *A61B 17/8869* (2013.01); *A61B 17/0467* (2013.01); *A61B 17/06* (2013.01); *A61B 17/82* (2013.01); *A61B 2017/0496* (2013.01)

(58) Field of Classification Search
CPC .... A61B 17/04; A61B 17/8869; A61B 17/06; A61B 17/0496; A61B 17/0469; A61B 2017/047; A61B 2017/0475; A61B 2017/06009; A61B 2017/06014; A61B 2017/06019; A61B 17/06061; A61B 17/8861; A61B 17/8872; A61B 17/8894; A61B 17/0401
USPC .......................................... 606/144–146, 148
See application file for complete search history.

(56) References Cited

U.S. PATENT DOCUMENTS 2,327,353 A * 8/1943 Karle ............................. 606/146
2,414,746 A * 1/1947 Karle ............................. 606/146
2,457,379 A * 12/1948 Kallenbach .................... 606/146
(Continued)

OTHER PUBLICATIONS

International Search Report and Written Opinion, mailed May 15, 2013, corresponding to PCT/US2013/021317, International Filing Date Jan. 11, 2013.

*Primary Examiner* — Jonathan W Miles
*Assistant Examiner* — Chima Igboko
(74) *Attorney, Agent, or Firm* — Donald E. Stout; Stout, Uxa & Buyan, LLP

(57) ABSTRACT

A system for repairing separated body tissues includes a tensioning device having a movable housing, a pair of stationary tensioning tips distal to and attached to the movable housing, and suture tensioning jaws on a proximal end of the movable housing. The tensioning jaws are pivotable between open and closed orientations. A buckle is provided for securing and tensioning suture and the like, having a first plate, a second plate spaced from the first plate so that there is a gap between the first and second plates, and a lock bar within the gap and movable between a first position wherein suture may be freely passed through the gap as tensioning of the suture proceeds, and a second locking position wherein the suture is clamped in place within the gap. A tension tab is provided for securing the lock bar in its first position until tension on the suture exceeds a predetermined level.

10 Claims, 10 Drawing Sheets

(51) Int. Cl.
*A61B 17/06* (2006.01)
*A61B 17/82* (2006.01)

(56) References Cited

U.S. PATENT DOCUMENTS

| | | | |
|---|---|---|---|
| 3,842,840 A * | 10/1974 | Schweizer | 606/145 |
| 3,959,960 A * | 6/1976 | Santos | 606/82 |
| 4,004,485 A * | 1/1977 | Hiscott | 84/207 |
| 4,617,933 A * | 10/1986 | Hasson | 606/190 |
| 4,832,666 A * | 5/1989 | Henderson | 474/135 |
| 4,890,615 A * | 1/1990 | Caspari et al. | 606/146 |
| 4,935,027 A * | 6/1990 | Yoon | 606/146 |
| 5,224,948 A * | 7/1993 | Abe et al. | 606/147 |
| 5,254,126 A * | 10/1993 | Filipi et al. | 606/146 |
| 5,336,229 A * | 8/1994 | Noda | 606/144 |
| 5,431,666 A * | 7/1995 | Sauer et al. | 606/139 |
| 5,527,322 A * | 6/1996 | Klein et al. | 606/144 |
| 5,755,729 A * | 5/1998 | de la Torre et al. | 606/148 |
| 5,797,927 A * | 8/1998 | Yoon | 606/144 |
| 5,993,467 A * | 11/1999 | Yoon | 606/147 |
| 6,017,358 A * | 1/2000 | Yoon et al. | 606/205 |
| 6,159,224 A * | 12/2000 | Yoon | 606/147 |
| 6,228,096 B1 * | 5/2001 | Marchand | 606/139 |
| 6,511,489 B2 * | 1/2003 | Field et al. | 606/148 |
| 6,527,785 B2 * | 3/2003 | Sancoff et al. | 606/148 |
| 6,663,643 B2 * | 12/2003 | Field et al. | 606/144 |
| 7,722,630 B1 * | 5/2010 | Stone et al. | 606/144 |
| 7,833,235 B2 * | 11/2010 | Chu | 606/144 |
| 7,879,046 B2 * | 2/2011 | Weinert et al. | 606/139 |
| 7,938,839 B2 * | 5/2011 | DiFrancesco et al. | 606/144 |
| 7,963,972 B2 * | 6/2011 | Foerster et al. | 606/139 |
| 8,052,696 B2 * | 11/2011 | Del Rio et al. | 606/144 |
| 8,303,591 B1 | 11/2012 | Foerster | |
| 8,414,599 B1 | 4/2013 | Foerster | |
| 8,496,674 B2 * | 7/2013 | Cabrera et al. | 606/144 |
| 8,888,849 B2 * | 11/2014 | Fallin et al. | 623/13.14 |
| 9,039,721 B2 * | 5/2015 | Ziniti et al. | 606/170 |
| 2002/0072753 A1 * | 6/2002 | Cohen | 606/103 |
| 2003/0050650 A1 * | 3/2003 | Field et al. | 606/144 |
| 2003/0208210 A1 * | 11/2003 | Dreyfuss et al. | 606/144 |
| 2004/0254592 A1 * | 12/2004 | DiCarlo et al. | 606/148 |
| 2004/0260314 A1 * | 12/2004 | Lizardi et al. | 606/144 |
| 2005/0049598 A1 * | 3/2005 | West et al. | 606/72 |
| 2005/0149066 A1 * | 7/2005 | Stafford | 606/144 |
| 2007/0225736 A1 * | 9/2007 | Zeiner et al. | 606/148 |
| 2008/0097483 A1 * | 4/2008 | Ortiz et al. | 606/148 |
| 2009/0082776 A1 * | 3/2009 | Cresina | 606/103 |
| 2009/0138048 A1 * | 5/2009 | Baccelli et al. | 606/263 |
| 2009/0182353 A1 * | 7/2009 | Snell et al. | 606/144 |
| 2009/0299409 A1 * | 12/2009 | Coe et al. | 606/232 |
| 2009/0312775 A1 * | 12/2009 | Gilkey et al. | 606/147 |
| 2009/0326563 A1 * | 12/2009 | White et al. | 606/148 |
| 2010/0042106 A1 * | 2/2010 | Bryant et al. | 606/103 |
| 2010/0049248 A1 * | 2/2010 | Del Rio et al. | 606/232 |
| 2010/0094314 A1 | 4/2010 | Hernlund et al. | |
| 2010/0228271 A1 * | 9/2010 | Marshall et al. | 606/144 |
| 2011/0022054 A1 * | 1/2011 | DiStefano et al. | 606/103 |
| 2011/0046645 A1 * | 2/2011 | McClurg et al. | 606/145 |
| 2011/0054493 A1 * | 3/2011 | McLean et al. | 606/139 |
| 2011/0112537 A1 * | 5/2011 | Bernstein et al. | 606/74 |
| 2011/0313435 A1 | 12/2011 | Aldridge et al. | |
| 2012/0010616 A1 | 1/2012 | Huang et al. | |
| 2012/0116421 A1 * | 5/2012 | Moon et al. | 606/144 |
| 2012/0123447 A1 * | 5/2012 | Corrao et al. | 606/144 |
| 2012/0232533 A1 * | 9/2012 | Veldman et al. | 606/1 |

* cited by examiner

ACTUATOR FOR BAND TENSIONING SYSTEM

This application claims the benefit under 35 U.S.C. 119(e) of the filing date of Provisional U.S. Application Ser. No. 61/586,566, entitled Actuator for Band Tensioning System, filed on Jan. 13, 2012, and expressly incorporated herein by reference, in its entirety.

This application is also related to U.S. patent application Ser. No. 12/347,821, entitled Dynamic Suture Tensioning Device and filed on Dec. 31, 2008, now allowed, to U.S. patent application Ser. No. 12/406,902, entitled Knotless Dynamic Suture Tensioning Device and Methods, filed on Mar. 18, 2009, to U.S. patent application Ser. No. 12/406,904, entitled Load Shaping for Dynamic Tensioning Mechanisms and Methods, filed on Mar. 18, 2009, now U.S. Pat. No. 8,303,591, to U.S. patent application Ser. No. 12/406,909, entitled Dynamic Tissue Holding Device with Low Profile Spring, filed on Mar. 18, 2009, to U.S. patent application Ser. No. 12/815,989, entitled Suture Band Buckle and Methods, filed on Jun. 15, 2010, to U.S. patent application Ser. No. 12/836,000, entitled Flat Suture Banding System and Methods, filed on Jul. 14, 2010, to U.S. patent application Ser. No. 12/858,332, entitled Low Friction Buckle Tightening System and Methods, filed on Aug. 17, 2010, and U.S. patent application Ser. No. 13/161,833, entitled Suture Buckle with Selective Friction, filed on Jun. 16, 2011, all of which are commonly assigned and expressly incorporated herein, by reference, in their entirety.

BACKGROUND OF THE INVENTION

The present invention is related to the general surgical repair of separated body tissues, and more particularly to internally fixating and stabilizing such body tissues, specifically bones.

In the present state of the art, there are a number of systems available to repair biological tissues separated in surgery or by injury. These products serve to approximate and stabilize the tissues so that healing may commence and provide compression in the interface to promote healing. Compression and stability are critical for proper anatomical healing of tissue. With the correct amount of compression applied to the interface of the tissue portions to be joined, signals are sent to the tissue, thus allowing the tissue to remodel in proper anatomical position. The amount of compression applied to the tissue interface needs to be appropriate to the type of tissue that is being healed.

Twisted wires are typically used to keep bone fragments together so they may heal. Twisted wires only hold tension as long as the twisted wire pair remains stable. Often the wires untwist too soon failing to keep the bone fragments together so that they may heal. Wires can also cut into the bone fragments allowing them to separate so that healing is difficult.

When it is necessary to access the thoracic cavity for a medical procedure, for example, it is required to cut the sternum into two pieces using a sternal saw. Once the procedure is completed within the thoracic cavity, the sternum must be repaired. For such repairs, it is known to use a dynamic compression device. Some of the drawbacks of this typical device, and others which are used include:

1. Bulky spring materials, while occupying substantial space, often do not store much energy. Some use polymer elastic bands, while other use coiled springs;

2. Wires are sometimes used to wrap the bones into position in compression with one another. However, wires can have sharp ends that can damage adjunctive tissues. Knot stacks in suture can interfere with the natural movement of surrounding tissues; and 3. Current banding systems that incorporate a biasing mechanism to achieve dynamic compression put the biasing mechanism in line with the band or suture. This practice competes with precious space at the healing site. Suture or bands are used to approximate tissues so that they may heal. It is desirable to obtain the best purchase possible on the tissue, so that the binding mechanics offered by the suture may be utilized. The best purchase is optimized by ensuring that the suture has the greatest contact area with the tissue. If a biasing mechanism is interfering with this concept, the biasing mechanism may diminish the suture's ability to hold the tissues together.

In addition, the current banding systems have stiff bands that are not compliant with bony undulations. Flat sutures are used, but are tedious to tie and do not hold reliably.

The banding systems of the present invention are therefore attractive for use in sternal closure because they offer some distinct advantages over the twisted wires most commonly used in the procedure.

Bands address the issues wires have in the following discussion. A band, by definition, is wide. In being wide, a band distributes its forces over a wider surface area. This inhibits the band from digging into the bone. In being wide, a band affords a larger cross-sectional area whereby more material may be realized thus presenting the opportunity to offer as much strength in the construct as is necessary to hold the bone fragments together. As such, bands address wire's two main weaknesses, namely, digging into the bone fragments being held together and, not having sufficient cross sectional area.

Bands bring in other attributes other than strength and reduced pressure on the bone. Some of these attributes are difficult to manage. With strength comes stiffness, as mentioned elsewhere herein. The larger cross-section of the band significantly increases the stiffness of the band. While stiffness and rigidity are good attributes in that they can stabilize the bone union, these attributes can also prevent the band from following the contours of the bone when inserted. This can lead to capturing tissues underneath the band that ultimately destabilize the union as the tissues continue to compress and disappear over time.

Binding the band ends together can also impose some problems. Generally this involves a mechanism on one band end that interfaces with holes or slots or contours on the other band end. This creates a tensioning system that is incremental in nature. As in the twisted wire system, this mechanical interface of the two ends is the weakest link in the system. This mechanical interface becomes stronger as the incremental steps become larger. But larger incremental steps aren't conducive to fine tuning the tension, so this is problematic. Flat sutures have been used to tie tissues together but the residual tension supplied in such a knotted structure is insufficient for optimum healing. There is a lot of fuss/time associated with trying to keep and hold a desirable tension with these flat sutures. What is needed is an attachment means that provides variable tensioning.

Another problem associated with all banding systems is that their tension holding capabilities are not sufficient for the environment in which they operate. Tension holding ability can be increased or enhanced by increasing friction at the binding interface of the band. What is needed however is a banding system with the ability to hold tension by selectively increasing friction at the binding interface during locking and/or after locking without increasing friction while tensioning.

What is needed, therefore, are improved devices and techniques for holding two tissue portions in a state of compression and tension that address and overcome these shortcomings in an innovative way.

SUMMARY OF THE INVENTION

The present invention solves the problems outlined above by providing a mechanized tensioning system for consistently and evenly applying a prescribed predetermined level of tension to the suture, at which point the suture is clamped in place within a buckle.

More particularly, there is provided a tensioning device comprising a housing movable axially between a distal rest position and a proximal tensioned position. A pair of stationary tensioning tips are disposed distally of the movable housing and attached thereto, and a mechanism is provided for moving the movable housing proximally away from its distal rest position toward its proximal tensioned position to tension suture disposed on the device. Tensioning jaws are disposed on a proximal end of the movable housing for securing suture therebetween, the tensioning jaws being pivotable between open and closed orientations respective to one another. In the illustrated embodiment, the mechanism comprises a ratcheting mechanism, for ensuring stepwise movement of the housing in a proximal direction without capability to move distally during a tensioning procedure. A release mechanism provides for releasing the housing and returning it to its distal rest position.

The tensioning device comprises an actuator for actuating the ratcheting mechanism to move the housing, which comprises a trigger in the illustrated embodiment. Advantageously, this actuator also actuates the tensioning jaws to pivot from their open orientation toward their closed orientation. A second actuator is provided for actuating the release mechanism to release the housing to its distal rest position, which also comprises a trigger in the illustrated embodiment. Advantageously, this second actuator also has a dual function, simultaneously releasing the tensioning jaws to return to their open orientation.

A second auxiliary mechanism for tensioning suture is also provided, which, as illustrated, comprises a thumb locking mechanism. While the primary ratcheting mechanism affords coarse tensioning adjustments to be made, the thumb locking mechanism offers fine tensioning adjustments, if desired.

In another aspect of the invention, there is provided a buckle apparatus for securing and tensioning suture and the like. This buckle apparatus comprises a first plate, a second plate spaced from the first plate so that there is a gap between the first and second plates, and a lock bar extending through the gap between the first plate and the second plate. The lock bar has a first position wherein suture may be freely passed through the gap as tensioning of the suture proceeds, and a second locking position wherein the suture is clamped in place within the gap. A tension tab is also provided. An end of the lock bar is engaged with the tension tab when the lock bar is in said first position. Movement of the tension tab when tension on the suture exceeds a predetermined level actuates the lock bar to the second locking position.

A spring connects the first and second plates, which preferably comprises a leaf spring. The tension tab includes a slot, and the lock bar end is engaged in the slot when the lock bar is in its first position. Movement of the tension tab when tension on the suture exceeds the aforementioned predetermined level, about 20 lb in one known embodiment, causes the lock bar end to disengage from the slot, thereby causing the lock bar to move into its second locking position.

In yet another aspect of the invention, there is provided a system for repairing separated body tissues, which comprises a tensioning device comprising a housing movable axially between a distal rest position and a proximal tensioned position, a pair of stationary tensioning tips disposed distally of the movable housing and attached thereto, and tensioning jaws disposed on a proximal end of the movable housing for securing suture therebetween. The tensioning jaws are pivotable between open and closed orientations respective to one another. The system further comprises a buckle apparatus for securing and tensioning suture and the like, comprising a first plate, a second plate spaced from the first plate so that there is a gap between the first and second plates, a lock bar within the gap and movable between a first position wherein suture may be freely passed through the gap as tensioning of the suture proceeds, and a second locking position wherein the suture is clamped in place within the gap. A tension tab is provided for securing the lock bar in its first position until tension on the suture exceeds a predetermined level.

The tensioning device further comprises a mechanism for moving the movable housing proximally away from its distal rest position toward its proximal tensioned position to tension suture disposed on the device and extending through said buckle apparatus. The mechanism comprises a ratcheting mechanism, for ensuring stepwise movement of the housing in a proximal direction without capability to move distally during a tensioning procedure. An actuator is provided for actuating the mechanism to move the housing. Advantageously, the actuator also actuates the tensioning jaws to pivot from their open orientation toward their closed orientation. The system further comprises a release mechanism for releasing the housing and returning it to its distal rest position. A second actuator is provided for actuating the release mechanism to release the housing to its distal rest position. Advantageously, the second actuator simultaneously releases the tensioning jaws to return to their open orientation.

In this system, an end of the lock bar is engaged with the tension tab when the lock bar is in its first position, and movement of the tension tab when tension on the suture exceeds the aforementioned predetermined level actuates the lock bar to the second locking position. The tension tab includes a slot, and the lock bar end is engaged in that slot when the lock bar is in its first position, wherein the movement of the tension tab when tension on the suture exceeds the predetermined level causes the lock bar end to disengage from the slot, thereby causing the lock bar to move into its second locking position.

In still another aspect of the invention, there is described a method for repairing separated body tissues, which comprises steps of passing a length of suture through a gap in a buckle, and extending a first end of the length of suture around a first stationary tensioning tip of a tensioning device and then proximally through an opening between two movable tensioning jaws at a proximal end of the tensioning device. A further step comprises extending a second end of the length of suture around a second stationary tensioning tip of a tensioning device and then proximally through the same opening between two movable tensioning jaws at a proximal end of the tensioning device. Further steps include tensioning the suture to a predetermined level, and moving a tension tab on the buckle, wherein movement of the tension tab actuates a locking bar to move to a position clamping the suture extending through the gap in the buckle.

The invention, together with additional features and advantages thereof, may best be understood by reference to the following description taken in conjunction with the accompanying illustrative drawings.

DESCRIPTION OF THE PREFERRED EMBODIMENT

Figure 1:
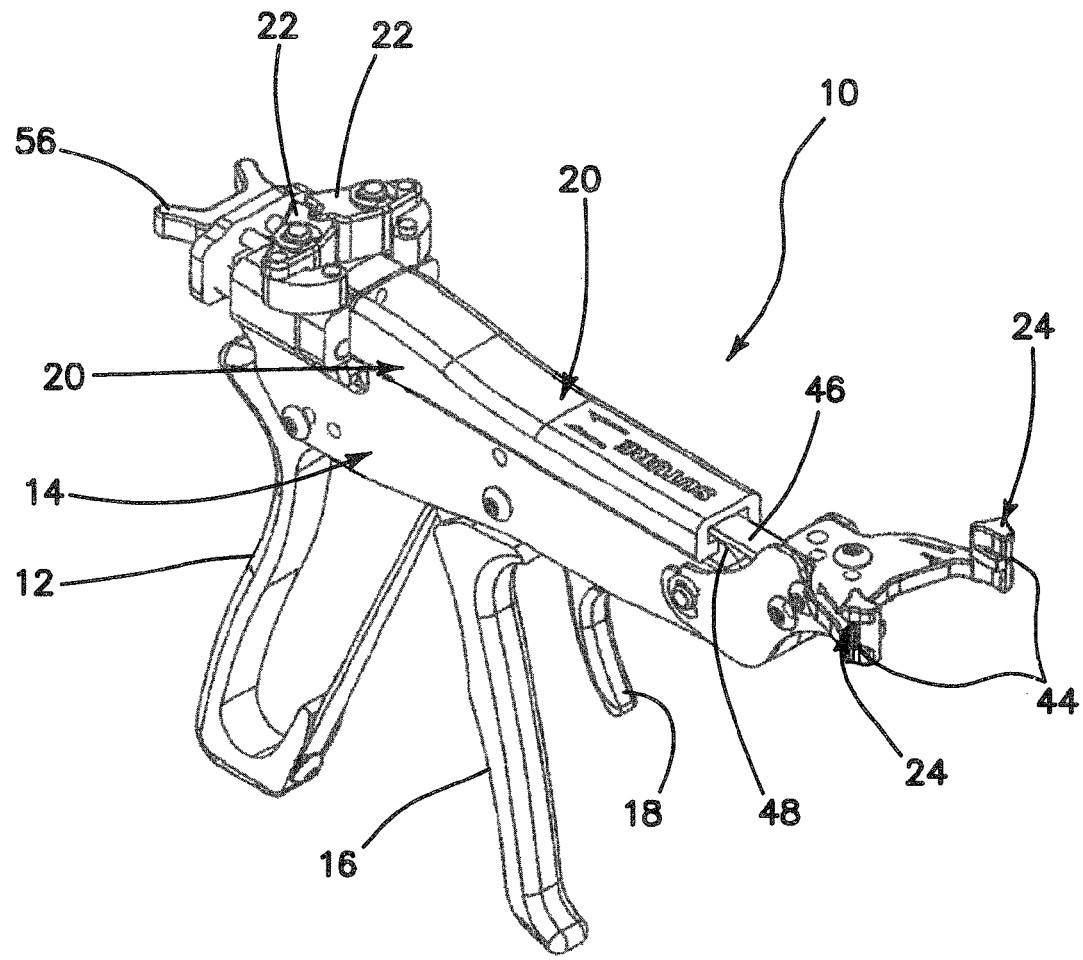
FIG. 1 is an isometric view of an actuator device constructed in accordance with the principles of the present invention.
Figure 2:
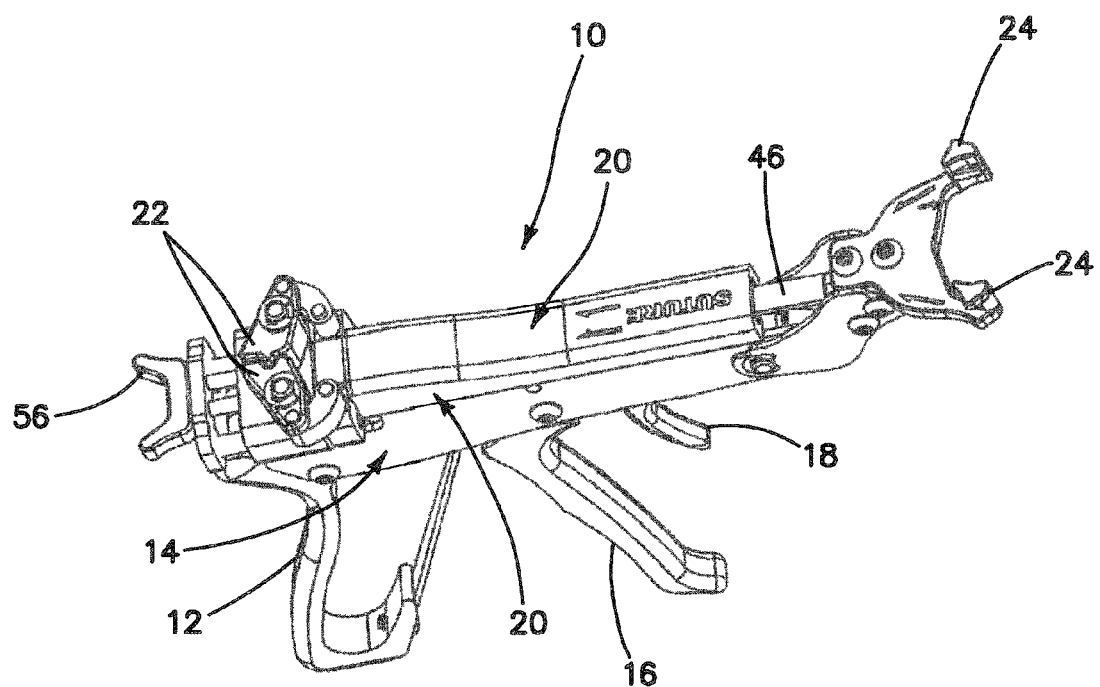
FIG. 2 is an isometric view of the device of FIG. 1, shown from a different orientation.
Figure 3:
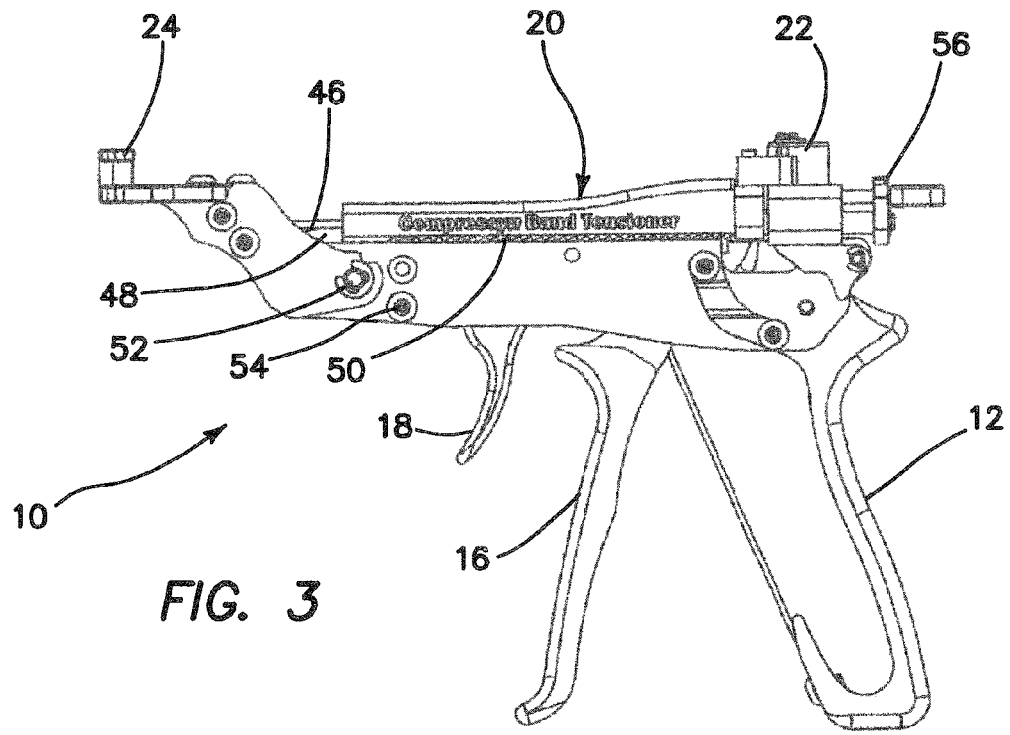
FIG. 3 is an elevation of the device of FIGS. 1 and 2.
Figure 4:
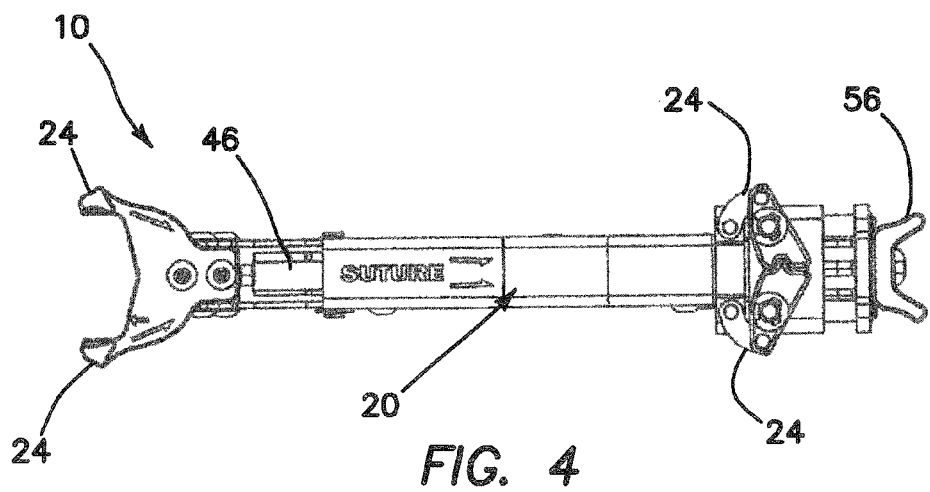
FIG. 4 is a top view of the device of FIG. 3.
Figure 6:
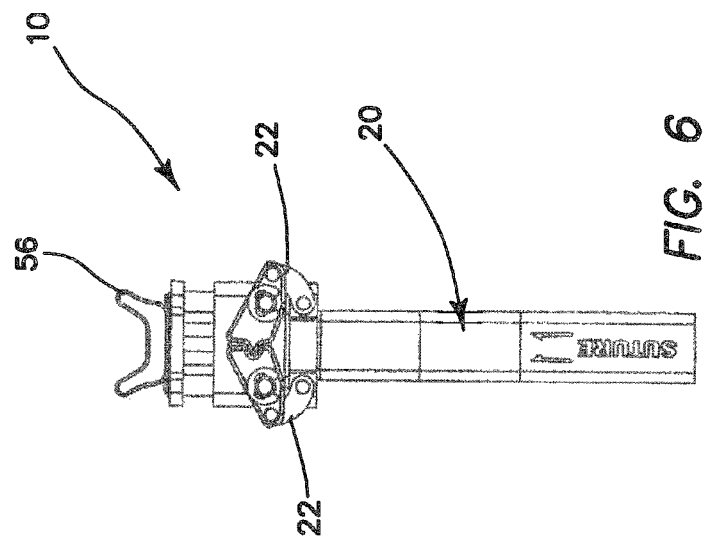
FIG. 6 is a top view of a ratchet mechanism forming a part of the device of FIGS. 1-5.

Referring more particularly to the drawings, a tensioning actuator 10 constructed according to the principles of the invention is shown and described. The actuator is constructed for easy and convenient gripping and operation by a practitioner, and comprises a grip or handle 12, a housing 14, a first longer trigger 16, and a second shorter trigger 18. Supported by the housing 14 is a movable housing 20, which is arranged to apply a tensioning force to suture, as will be described below. Additional features of the actuator 10 include tensioning jaws 22 and tensioning tips 24.

FIGS. 7-13 illustrate a buckle apparatus 26 for securing and tensioning suture, in the form of a compression band or strap having, in certain embodiments, a width of approximately 5 mm, for the purpose of securing bone fragments together until they knit and heal in place. The buckle 26 comprises first and second spaced plates 28, a leaf spring 30, a lock bar 32, and a tension tab 34.

Figure 13:
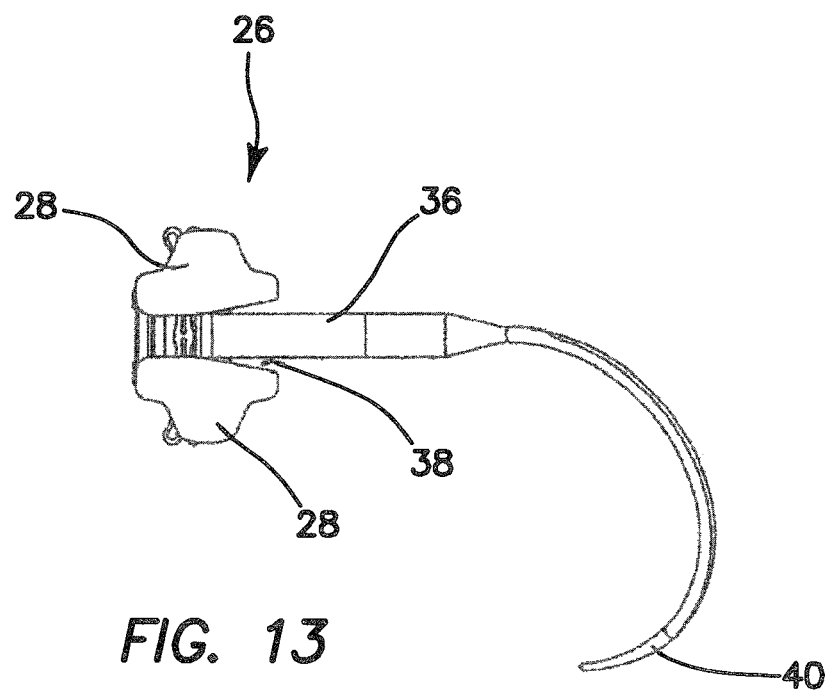
FIG. 13 is a rear view of the buckle and suture band of FIG. 7.
Figure 8:
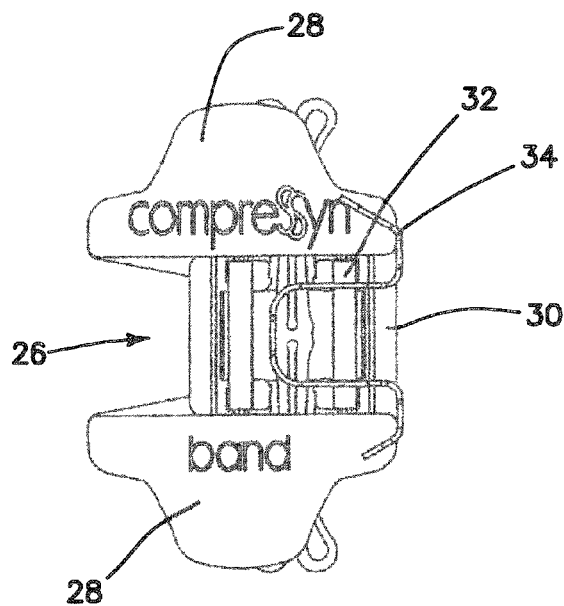
FIG. 8 is a front view of the buckle of FIG. 7.
Figure 9:
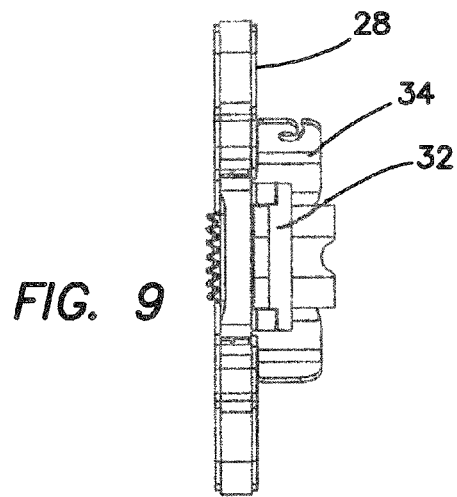
FIG. 9 is a left-side view of the buckle of FIGS. 7 and 8.
Figure 10:
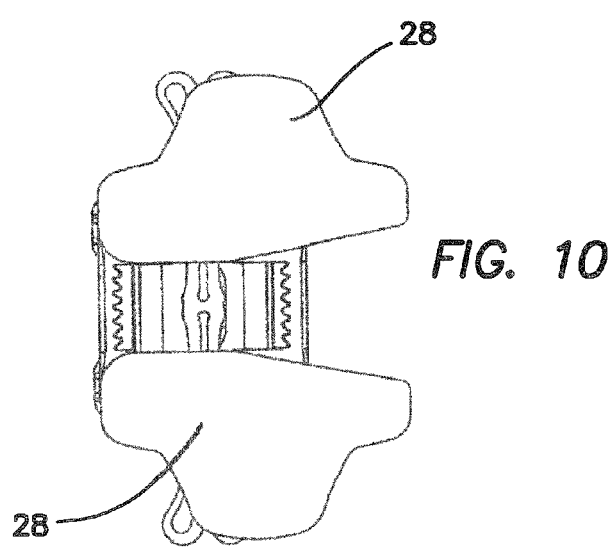
FIG. 10 is a rear view of the buckle of FIG. 7.
Figure 12:
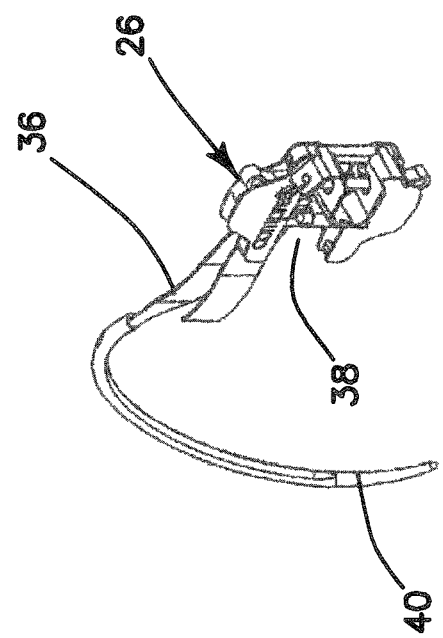
FIG. 12 is an isometric view of the buckle and suture band of FIG. 11.
Figure 11:
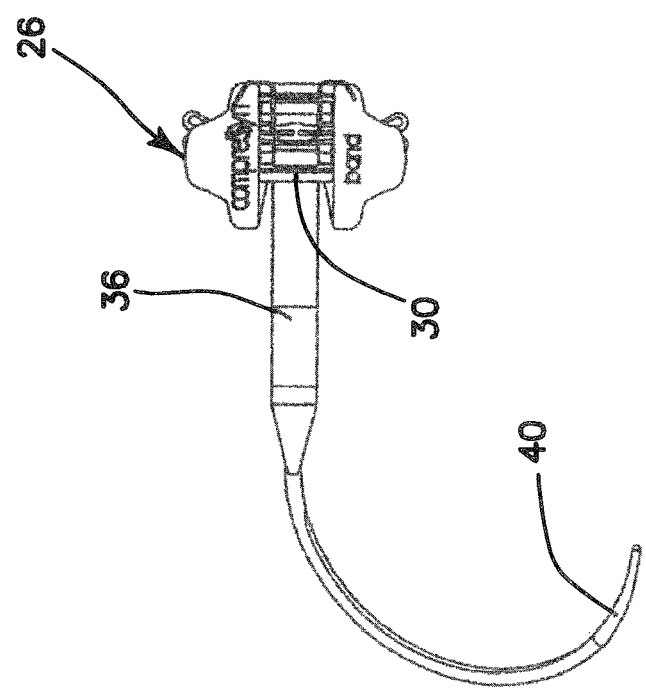
FIG. 11 is a front view of the buckle of FIG. 7 with a suture band installed.
Figure 14:
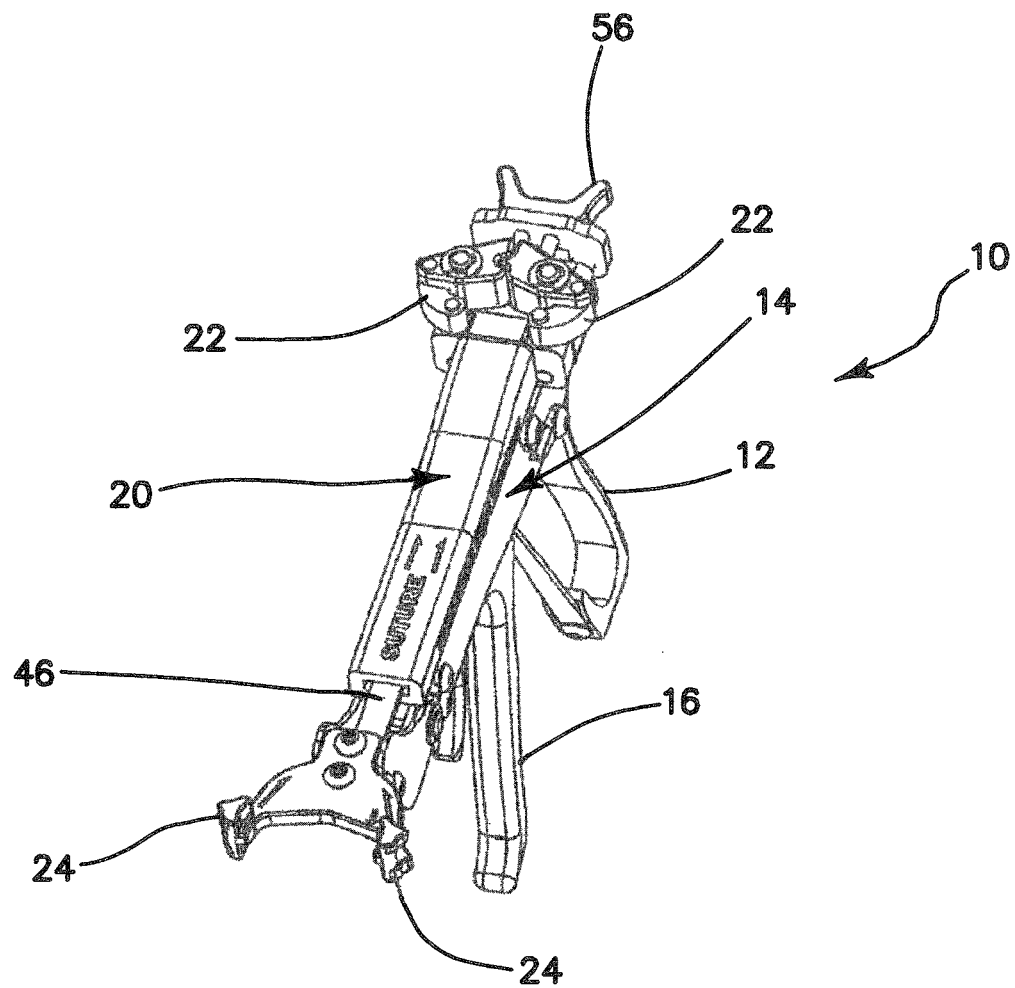
FIG. 14 is an isometric view of the device of FIG. 1, wherein the tensioner jaws are shown in a closed orientation.

In FIGS. 11-13, a suture band 36 is shown extending through a gap 38 between the plates 28 of the buckle 26. A needle 40 is disposed on the end of the suture band 36 for penetrating bone and tissue, as necessary. In practice, the suture band 36 is positioned as desired around bone to be repaired, and is then tensioned to tighten the band around the bone in order to secure the bone in proper position, and to ensure that the band will remain in tension during the entire healing process, by ensuring that the implant follows the bone as it shrinks during healing. During this tensioning step, the lock bar 32 remains in its unactuated position, permitting free movement of the suture band 36 through the gap 38 in the buckle as the tensioning proceeds. The lock bar 32, in fact, is restrained from moving to its locking position by engagement of one end of the lock bar 32 with a slot 42 in the tension tab 34. When a predetermined tensioning force is applied to the suture band 36, approximately 20 lb in one embodiment, the friction forces restraining the lock bar 32 are overcome, and the lock bar pops out of the slot 42. This locks the buckle in place, preventing further movement of the suture band 36.

Figure 5:
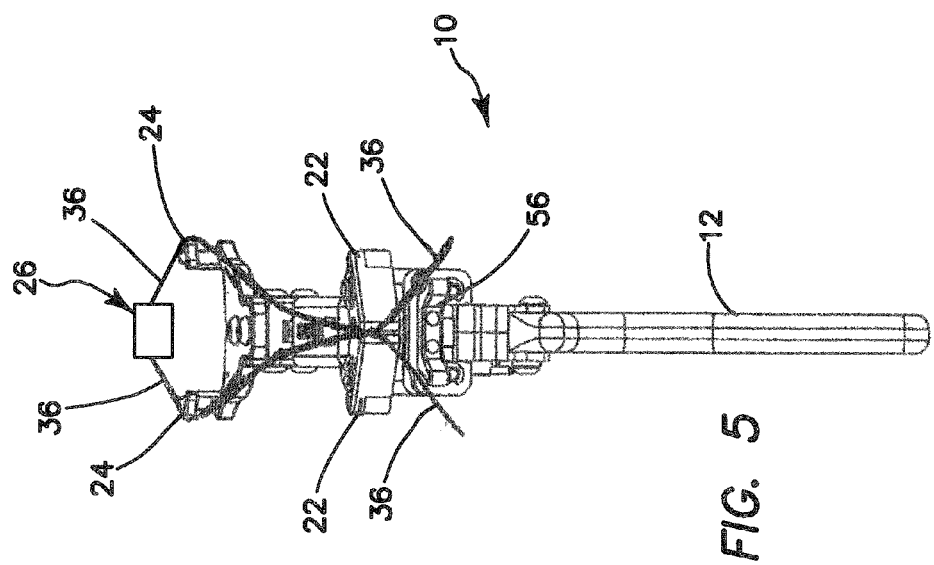
FIG. 5 is a rear view of the device of FIG. 4.
Figure 7:
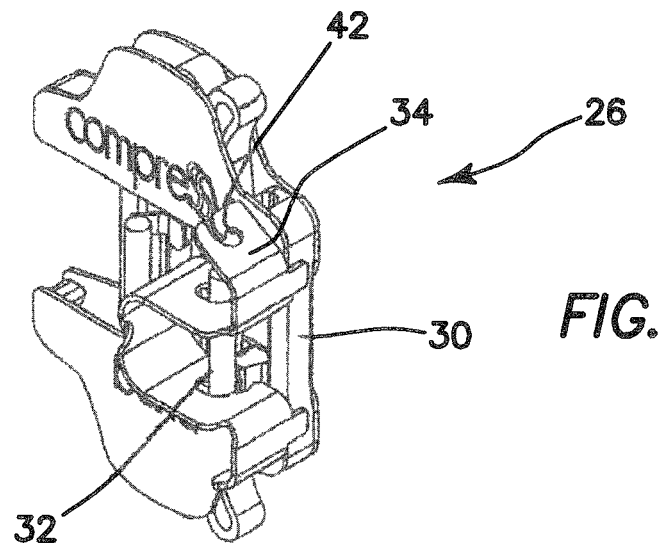
FIG. 7 is an isometric view of a buckle for tensioning a band constructed and installed in accordance with the principles of the present invention.

In practice, while this arrangement is an excellent solution to the issue of effective management and healing of the procedural site, it is difficult to manually apply the required amount of force to clamp the suture in place. Thus, the actuator 10, described above and illustrated in FIGS. 1-6 and 14-16, is employed to easily and smoothly apply the required tension. In FIG. 5, the buckle apparatus 26 is shown schematically, with the associated suture band 36, for the purpose of illustrating how the actuator 10 is used in conjunction with the buckle 26 to tension the suture at the procedural site. Specifically, as shown, each end of the suture band 36, extending from opposite sides of the buckle 26, passes around its respective tensioning tip 24, seated in suture grooves 44 (FIG. 1) disposed on those tips 24. The suture bands 36 then extend along the top surface of the movable housing 20, and through the gap between the tensioning jaws 22, which are in the open position shown in FIG. 16 in this rest orientation. Because the suture is guided around each of the tensioning tips 24 in the channels 44, and is further guided into the gap between the jaws 22, it naturally lies directly atop the movable housing 20. No threading is necessary.

A mounting shaft 46 extends distally from the movable housing 20 to support the stationary distal tensioning tips 24. A spring coil release 48 (FIG. 1) is associated with the shaft 46 for returning the movable housing 20 to its rest position, which is the position shown in FIG. 16, with the tensioning jaws 22 in their open position. In this rest position, the movable housing 20 is at its closest position relative to the tensioning tips 24, as shown in FIG. 16.

Figure 15:
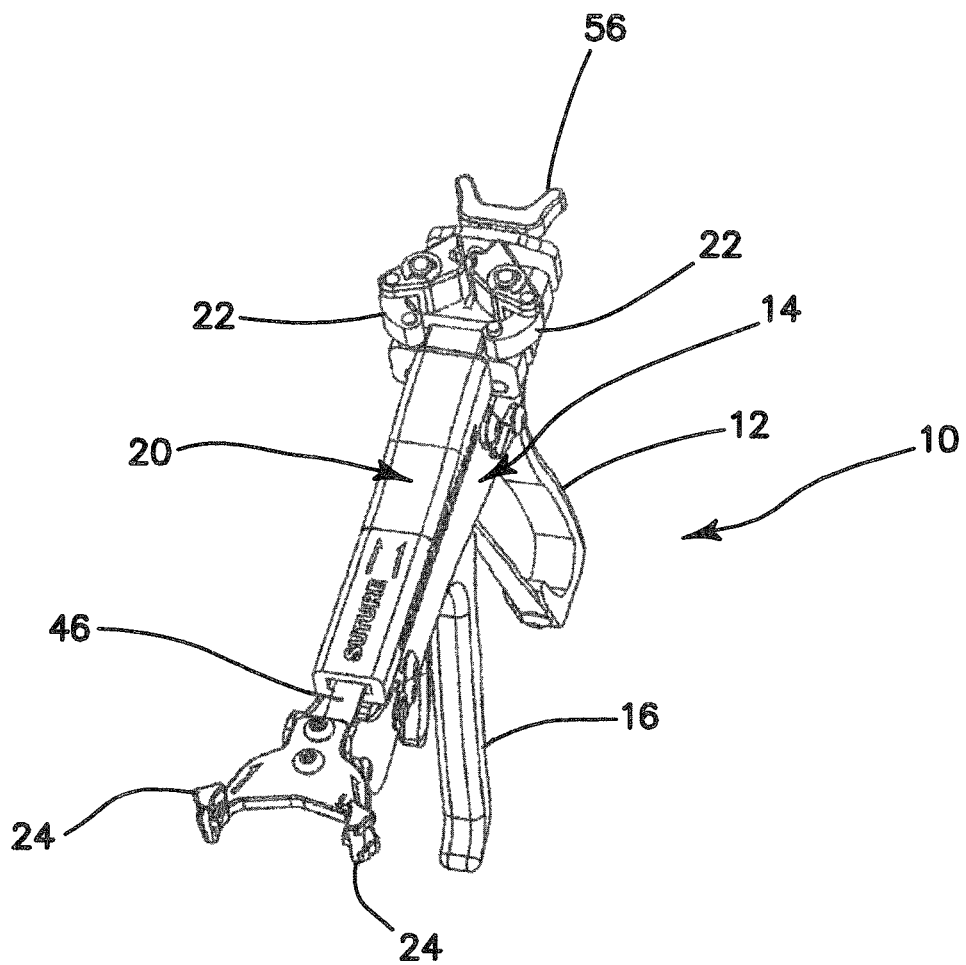
FIG. 15 is an isometric view similar to that of FIG. 14, wherein the tensioner jaws are shown in a partially open orientation.

When it is desired to apply a tensioning force to the two suture band ends 36 disposed about each of the tensioning tips 24 and over the housing 20, the trigger 16 is squeezed or actuated by the operator, which in turn actuates ratcheted gears 50 (FIG. 3) beneath the housing to move the housing proximally, away from the tensioning tips 24 in stepwise fashion. The trigger may be repeatedly actuated, moving the housing 20 proximally the distance between adjacent ratchet teeth with each actuation. Importantly, with the use of a ratcheting system, return movement of the housing toward the tensioning tips 24 is prevented, thus ensuring that increasing tension is evenly applied to the suture as the process continues. With the commencement of the ratcheting/tensioning process, as shown in FIG. 15, the tensioning jaws 22 move to a transitional mid-open orientation, and it can be seen from that same figure that the exposed portion of the shaft 46 is lengthening as the housing 20 moves proximally away from the tensioning tips 24. Within a few squeezes of the trigger 16, the jaws 22 continue automatically to move to the fully closed orientation (FIG. 14) as the tensioning process continues.

As the applied tensioning force reaches its predetermined level, which is 20 lb in one exemplary embodiment, the lock bar 32 is released from the tensioning tab 34 of the buckle 26 to actuate the buckle to a locked orientation. This locks the suture 36 in place within the clamp.

Figure 16:
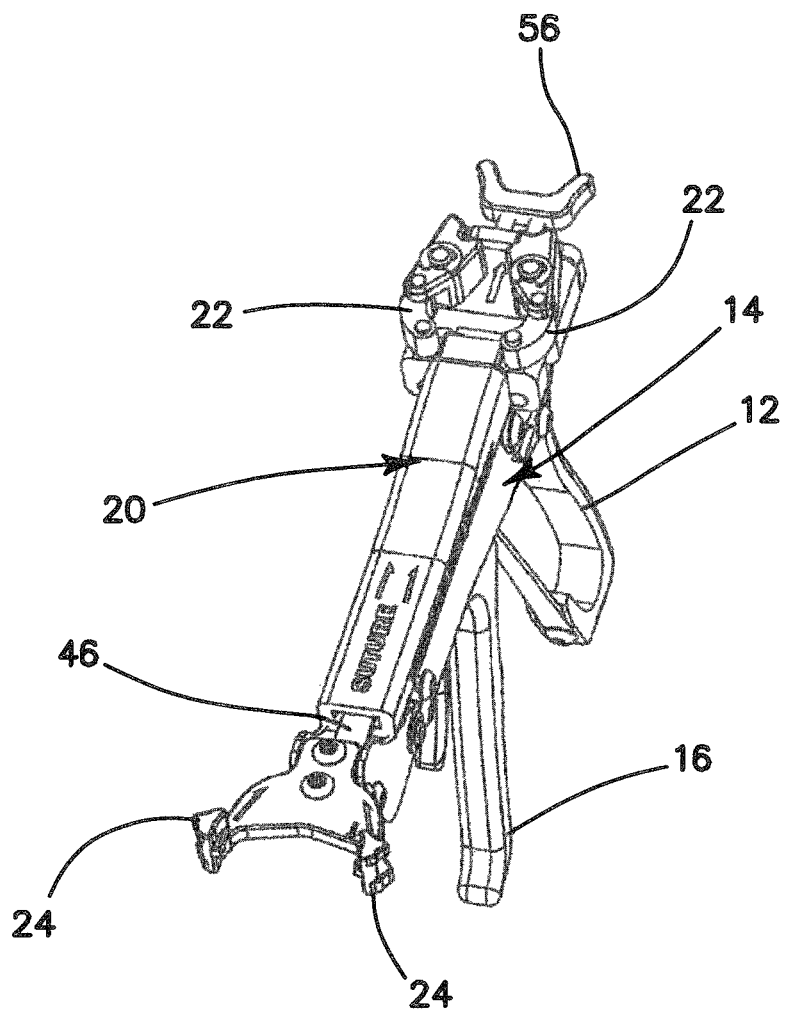
FIG. 16 is an isometric view similar to those of FIGS. 14 and 15, wherein the tensioner jaws are shown in an open orientation.

Once the procedure is completed, and the suture clamped securely in place, the second trigger 18 may be actuated, which releases the pivoting jaws 22 to their open position, and simultaneously activates the spring coil release 48 to return the housing 20 to its rest position (FIG. 16). At this point, the procedure is complete, the suture may be removed from the actuator 10 and cut and tied off, as appropriate, and the actuator 10 removed from the procedural site.

Additional advantageous features of the inventive tensioning actuator 10 are as follows. Because of the two spaced, stationary tensioning tips 24, providing two pivot points for the two suture band ends, a lateral, even pull is applied to the two pieces of suture band 36, to ensure an even tensioning of the band and sufficient applied tension to activate the implant. The actuator is arranged and designed to provide a convenient sight line down the axis of the actuator, from its proximal end to assist the practitioner in completing a quick deployment and an easy on and off procedure. A hinge 52, which may be released by an adjacent button 54, or other suitable means, is provided to permit the distal end of the actuator 10, including the distal tensioning tips 24, to be pivoted downwardly relative to the housing 20, in order to permit cleaning and other repairs to be made. The suture contact surfaces of the tensioning jaws 22 are appropriate textured to prevent cutting or fraying of the suture 36.

Another advantageous feature, at the proximal end of the actuator 10, is a thumb locking mechanism 56, which provides a secondary means of deploying or locking the suture tensioning mechanism. This mechanism 56 may provide a finer adjustment than the primary suture tensioning mechanism actuated by the trigger 16.

It should be noted that, though the tensioning tips 24 are locked into a stationary configuration during a particular tensioning procedure, they may be unlocked and moved outwardly or inwardly, as desired, to adapt the tensioning device 10 to various applications and uses with variously sized implants, and for applying differing levels of predetermined actuation tensioning levels and leverage. Although an exemplary implant 26 has been shown and described sufficiently for the purpose of explaining the function of the actuator 10, the actuator 10 is adapted for use in any application requiring the application of an even and definable tensile force to two ends of suture, cord, bands, or any other type of securing device.

Additionally, while the inventive concept has been particularly developed and adapted for use in repairing the sternum after a thoracic cavity procedure, it is, of course, applicable to a great many other procedures requiring repair of bodily tissue, particularly bone. In addition, the invention is applicable to other non-surgical environments as well.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention, which is to be limited only in accordance with the following claims.

What is claimed is:

1. A buckle apparatus for securing and tensioning suture and the like, comprising:
    a first plate;
    a second plate spaced from said first plate so that there is a gap between said first and second plates;
    a lock bar extending through said gap between said first plate and said second plate and having a first position wherein suture may be freely passed through said gap as tensioning of the suture proceeds, and a second locking position wherein the suture is clamped in place within said gap;
    a tension tab;
    wherein an end of the lock bar is engaged with the tension tab when the lock bar is in said first position, and movement of the tension tab when tension on said suture exceeds a predetermined level actuates said lock bar to the second locking position;
    a leaf spring connecting said first and second plates;
    wherein said tension tab includes a slot and the lock bar end is engaged in said slot when the lock bar is in its first position, and further wherein the movement of the tension tab when tension on said suture exceeds said predetermined level causes the lock bar end to disengage from said slot, thereby causing the lock bar to move into its second locking position.

2. The buckle apparatus as recited in claim 1, wherein the predetermined tension level comprises approximately 20 lb.

3. A system for repairing separated body tissues, comprising:
    a tensioning device comprising a housing movable axially between a distal rest position and a proximal tensioned position, a pair of stationary tensioning tips disposed distally of the movable housing and attached thereto, and tensioning jaws disposed on a proximal end of the movable housing for securing suture therebetween, the tensioning jaws being pivotable between open and closed orientations respective to one another; and
    a buckle apparatus for securing and tensioning suture and the like, comprising a first plate, a second plate spaced from the first plate so that there is a gap between the first and second plates, a lock bar within said gap and movable between a first position wherein suture may be freely passed through the gap as tensioning of the suture proceeds, and a second locking position wherein the suture is clamped in place within the gap, and a tension tab for securing the lock bar in its first position until tension on the suture exceeds a predetermined level;
    wherein an end of the lock bar is engaged with the tension tab when the lock bar is in its first position, and movement of the tension tab when tension on the suture exceeds said predetermined level actuates the lock bar to the second locking position.

4. The system as recited in claim 3, wherein said tensioning device further comprises a mechanism for moving the movable housing proximally away from its distal rest position toward its proximal tensioned position to tension suture disposed on the device and extending through said buckle apparatus.

5. The system as recited in claim 4, wherein said mechanism comprises a ratcheting mechanism, for ensuring stepwise movement of the housing in a proximal direction without capability to move distally during a tensioning procedure.

6. The system as recited in claim 4, and further comprising an actuator for actuating the mechanism to move the housing.

7. The system as recited in claim 6, wherein said actuator also actuates the tensioning jaws to pivot from their open orientation toward their closed orientation.

8. The system as recited in claim 4, and further comprising:
    a release mechanism for releasing the housing and returning it to its distal rest position; and
    a second actuator for actuating the release mechanism to release said housing to its distal rest position.

9. The system as recited in claim 8, wherein the second actuator simultaneously releases the tensioning jaws to return to their open orientation.

10. The system as recited in claim 3, wherein said tension tab includes a slot and the lock bar end is engaged in said slot when the lock bar is in its first position, wherein the movement of the tension tab when tension on the suture exceeds said predetermined level causes the lock bar end to disengage from the slot, thereby causing the lock bar to move into its second locking position.

* * * * *